US012734044B2

(12) United States Patent
Colleran et al.

(10) Patent No.: US 12,734,044 B2
(45) Date of Patent: Sep. 15, 2026

(54) DEVICES AND METHODS FOR TISSUE TRANSFER

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Dennis P. Colleran, Memphis, TN (US); Ali Hosseini, Memphis, TN (US); Nehal N. Patel, Memphis, TN (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 231 days.

(21) Appl. No.: 18/713,032

(22) PCT Filed: Nov. 18, 2022

(86) PCT No.: PCT/US2022/050354
§ 371 (c)(1),
(2) Date: May 23, 2024

(87) PCT Pub. No.: WO2023/096828
PCT Pub. Date: Jun. 1, 2023

(65) Prior Publication Data

US 2025/0017617 A1 Jan. 16, 2025

Related U.S. Application Data

(60) Provisional application No. 63/345,628, filed on May 25, 2022, provisional application No. 63/285,720, (Continued)

(51) Int. Cl.
*A61F 2/46* (2006.01)
*A61B 17/3205* (2006.01)

(52) U.S. Cl.
CPC ...... *A61F 2/4601* (2013.01); *A61B 17/32053* (2013.01)

(58) Field of Classification Search
CPC ........................ A61F 2/4601; A61B 17/32053
See application file for complete search history.

(56) References Cited

U.S. PATENT DOCUMENTS 6,796,987 B2 * 9/2004 Tague ................ A61B 17/8822 606/94
2004/0034434 A1 * 2/2004 Evans ..................... A61P 19/08 623/23.51

(Continued)

FOREIGN PATENT DOCUMENTS

DE 20109331 * 8/2001 ........... A61B 10/025

OTHER PUBLICATIONS

International Written Opinion corresponding to related International Patent Application No. PCT/US2022/050354, mailed May 25, 2023, 6 pages. (Year: 2023).*

*Primary Examiner* — Christian A Sevilla
(74) *Attorney, Agent, or Firm* — ArentFox Schiff LLP; Joseph M. Maraia

(57) ABSTRACT

A tissue transfer device includes a handle and a chisel attached to the handle. A pusher rod or tamp extends through the chisel and is axially moveable relative to the chisel. A control mechanism coupled to the handle moves the tamp distally relative to the outer tube to expel a tissue graft from the chisel in a controlled manner. The tamp has a measurement scale that allows the user to leave the harvested graft in the harvest tool during measurement.

8 Claims, 17 Drawing Sheets

Related U.S. Application Data filed on Dec. 3, 2021, provisional application No. 63/282,723, filed on Nov. 24, 2021, provisional application No. 63/282,722, filed on Nov. 24, 2021.

(56) References Cited

U.S. PATENT DOCUMENTS

| | | | | |
|---|---|---|---|---|
| 2006/0178748 | A1* | 8/2006 | Dinger, III | A61B 17/1615 623/18.11 |
| 2007/0262116 | A1* | 11/2007 | Hueil | A61B 17/07207 227/175.1 |
| 2008/0195115 | A1* | 8/2008 | Oren | A61F 2/4618 81/488 |
| 2011/0306983 | A1* | 12/2011 | O'Halloran | A61B 17/8822 606/94 |
| 2019/0167444 | A1* | 6/2019 | Behzadi | A61F 2/28 |
| 2020/0146737 | A1* | 5/2020 | Alleyne | A61B 17/8822 |

* cited by examiner

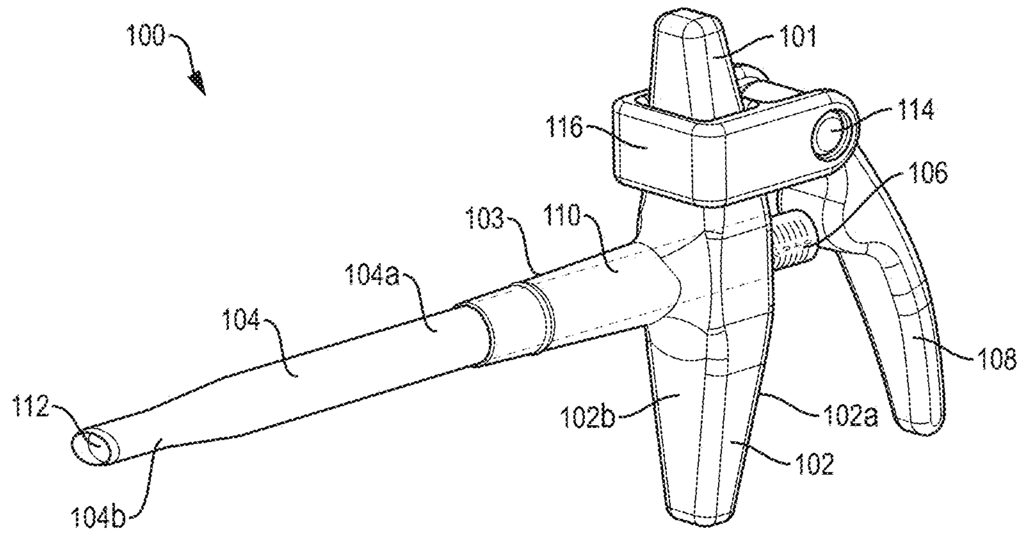
FIG. 1A
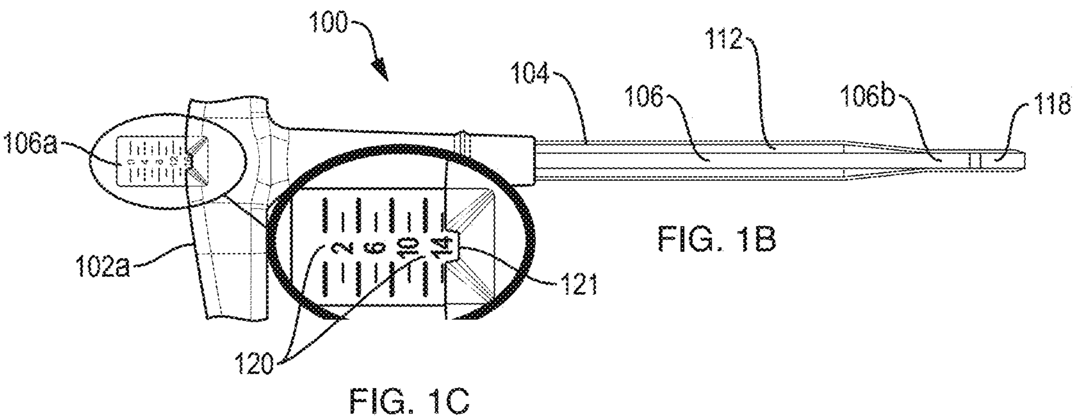
FIG. 1B
FIG. 1C 108
106
102
124
118

108
106
106
126
118
124

124
118

106
106a
118

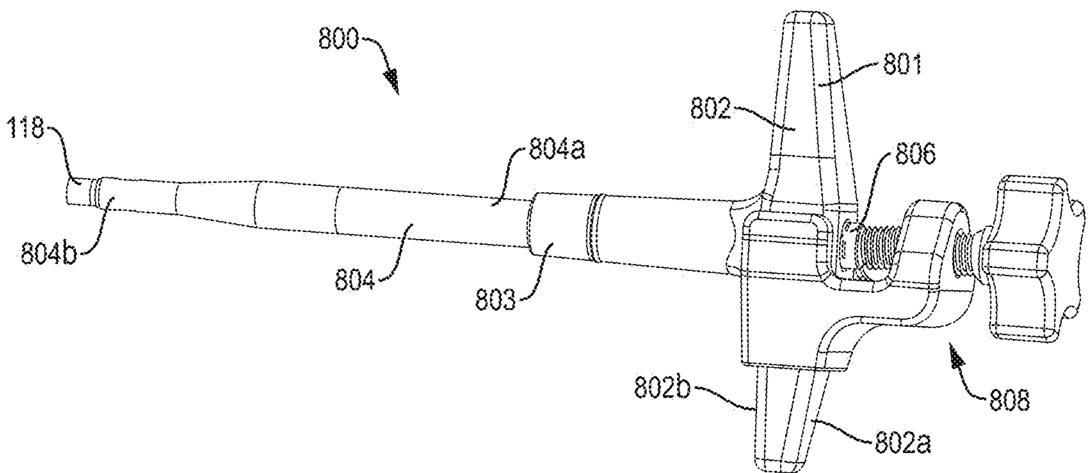
FIG. 11A
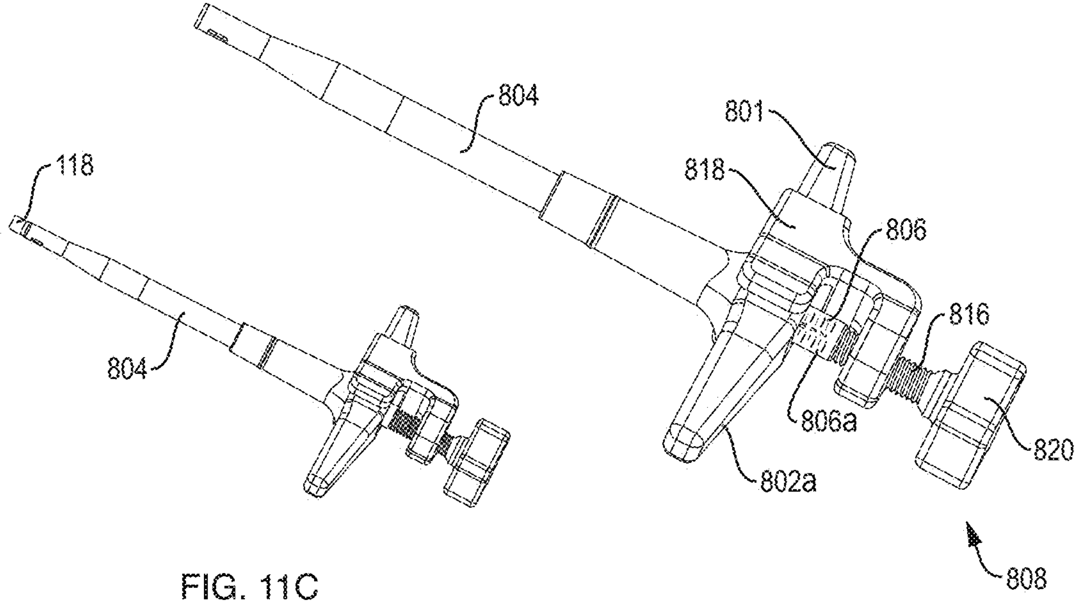
FIG. 11C
FIG. 11B

DEVICES AND METHODS FOR TISSUE TRANSFER

CROSS-REFERENCE TO RELATED APPLICATIONS

This application is the U.S. national phase entry under 35 U.S.C. § 371 of International Application No. PCT/US2022/050354, filed Nov. 18, 2022, entitled DEVICES AND METHODS FOR TISSUE TRANSFER, which in turn claims priority to and benefit of U.S. Provisional Application No. 63/282,722, filed Nov. 24, 2021, U.S. Provisional Application No. 63/282,723, filed Nov. 24, 2021, U.S. Provisional Application No. 63/285,720, filed Dec. 3, 2021, and U.S. Provisional Application No. 63/345,628, filed May 25, 2022, the contents of which are incorporated herein by reference in their entirety for all purposes.

FIELD

The present disclosure relates to tissue transfer devices and, more particularly, to devices and methods for surgical repair of a defect in articular cartilage.

BACKGROUND

Damage to articular cartilage can result from several causes, such as sports injuries, accidents, or wear and tear over time. Surgeons use several procedures for repairing articular cartilage. One surgical procedure includes taking a cartilage graft from a non-weight bearing part of a joint and transferring the graft to the defect area. In such procedures, surgeons must gently handle the donor graft to maximize graft viability. However, many current techniques use a mallet to deliver the graft, which can harm the viability of the graft.

Another challenge with current cartilage repair techniques involves the proper measurement of the harvested graft. The harvest tool usually has a scale to predict the graft length prior to cutting. However, often the graft does not break cleanly and the actual graft height differs from the expected or planned length. Therefore, to determine graft length, many surgeons use a scale to measure the graft after harvesting. Using a scale requires removal of the graft from the harvest tool and placement of the graft into a delivery tool. Such methods are inefficient and could contaminate the graft.

Additional problems occur when the donor graft topography does not match the topography of the recipient hole as closely as possible. This results in a placed graft that has a discontinuous surface relative to the surrounding cartilage. For example, the graft may have one side that sits proud to the surrounding cartilage and an opposite side that sits below the surface of the surrounding cartilage. In the first scenario, the graft produces a catching motion, while in the second, the graft cannot provide proper support. Current techniques require the user to visually estimate alignment, which can lead to much variation from the desired orientation. Further problems arise when a surgeon attempts to match the depth of the recipient hole at various locations around the hole, which often requires multiple measurements, leading to inaccuracies in hole measurements.

SUMMARY

The disclosure describes a tissue transfer device including a handle a chisel attached to the handle. A pusher rod or tamp extends through the chisel and is axially moveable relative to the chisel. A control mechanism coupled to the handle moves the tamp distally relative to the chisel to expel a tissue graft from the chisel in a controlled manner. The tamp has a measurement scale that allows the user to leave the harvested graft in the harvest tool during measurement, thus eliminating the need to remove the graft. This advantageously reduces surgical time and keeps the donor graft in a clean, aseptic environment until delivery.

The disclosure also describes alignment guides for use with the tissue transfer device of this disclosure. The alignment guides can be integral with or attached to the device or to a guidewire to prepare the repair site or harvest the donor graft. The alignment guides have multiple indicators that, when in equal contact with a tissue surface, indicate to the user that the tissue transfer device or guidewire is perpendicular to that surface. When the indicators are not in equal contact, the guides alert the user to change the orientation of the tissue transfer device or guidewire to gain proper alignment.

The disclosure also describes tools for measuring a depth of a recipient hole at various locations around the hole in a single step.

The disclosure also describes tools for creating a hole in an area of a tissue defect to a depth pre-selected to be equal to a length of a tissue graft.

Further examples of the tissue transfer device and methods of use of this disclosure may include one or more of the following, in any suitable combination.

Examples of a tissue transfer device of this disclosure include a handle having a first surface and a second surface opposite the first surface. A through hole defined by the handle extends through a width of the handle. An outer tube has a proximal end, a distal end, and a cannulation extending between the proximal and distal ends. The proximal end couples to the second surface of the handle such that the cannulation extends in line with the through hole. The distal end is configured for insertion into tissue. An inner shaft extends through the cannulation of the outer tube such that a proximal end of the inner shaft projects from the first surface of the handle. The inner shaft is axially moveable relative to the outer tube. A control mechanism couples to the handle. The control mechanism is configured to move the inner shaft distally relative to the outer tube to expel a tissue graft from the outer tube.

In further examples, the control mechanism is one of a lever arm, a ratchet mechanism or a screw mechanism. In examples, the proximal end of the inner shaft comprises indicia corresponding to a length of the tissue graft. In examples, the distal end of the outer tube defines a window for direct visualization of the expulsion of the tissue graft. In examples, the inner shaft is removeable from the cannulation of the outer tube and configured to be used as a tamping tool. In examples, a diameter of the proximal end of the inner shaft is selected to be wider than an inner diameter of the cannulation such that, when the inner shaft is fully inserted into the outer tube, the proximal end contacts the first surface of the handle.

Examples of methods of a tissue repair of this disclosure include creating a hole in an area of a tissue defect. A distal end of an outer tube of a tissue transfer device is inserted into an area of healthy tissue such that a tissue graft enters the distal end. The tissue transfer device further includes a handle having a first surface and a second surface opposite the first surface. A through hole defined by the handle extends through a width of the handle. The outer tube further has a proximal end and a cannulation extending between the proximal and distal ends. The proximal end couples to the second surface of the handle such that the cannulation extends in line with the through hole. An inner shaft extends through the cannulation of the outer tube such that a proximal end of the inner shaft projects from the first surface of the handle. The inner shaft is axially moveable relative to the outer tube. A control mechanism couples to the handle in contact with the proximal end of the inner shaft. The method also includes inserting the distal end of the outer tube into the hole. An inner shaft is inserted through the cannulation of the outer tube such that a proximal end of the inner shaft projects from the first surface of the handle. Using the control mechanism, the inner shaft is moved distally relative to the outer tube to expel the tissue graft into the hole.

In further examples, the control mechanism is one of a lever arm, a ratchet mechanism or a screw mechanism. In examples, the method further includes measuring a length of the tissue graft using indicia on a surface of the proximal end of the inner shaft, the indicia corresponding to the length of the tissue graft. In examples, the method further includes removing the inner shaft from the cannulation of the outer tube and tamping the tissue graft into the hole with the proximal end of the outer tube. In examples, the method further includes, before using the control mechanism, coupling the control mechanism to the handle. In examples, the method further includes after creating the hole in the area of the tissue defect, measuring the hole at a plurality of locations about the hole with a measuring tool. The measuring at the plurality of locations occurs substantially simultaneously.

Examples of an alignment guide for determining an orientation of a surgical instrument of this disclosure include an elongated body having a distal surface, a proximal surface opposite the distal surface, and a central bore defined by an outer wall extending between the proximal and distal surfaces. The central bore is configured for passage of the surgical instrument. A plurality of linear channels defined by the outer wall extend at least partially along the outer wall. A plurality of pins operatively couple to the body. Each one of the plurality of pins is independently slidable within a respective one of the plurality of channels. Each one of the plurality of pins includes a first end configured to extend from the distal surface of the body to contact tissue, and an indicator coupled to a second end of each one of the plurality of pins. The indicator extends outside of the elongated body. In further examples, the indicator is a second end of the pin extending from the proximal surface of the body. In other examples, the indicator is a fin extending from the outer wall at a distal end of the elongated body. In examples, the surgical instrument is one of a tissue transfer device or a guidewire.

A reading of the following detailed description and a review of the associated drawings will make apparent the advantages of these and other features. Both the foregoing general description and the following detailed description serve as an explanation only and do not restrict aspects of the disclosure as claimed.

BRIEF DESCRIPTION OF THE DRAWINGS

Reference to the detailed description, combined with the following figures, will make the disclosure more fully understood, wherein:

FIG. 1A is a perspective view of an example of the tissue transfer device of this disclosure;

FIG. 1B is a cross-sectional view of the outer tube of the tissue transfer device of FIG. 1A;

FIG. 1C is a detailed view of the proximal end of the inner shaft of the tissue transfer device of FIG. 1A;

FIGS. 11A-C illustrate another example of the tissue transfer device of this disclosure.

DETAILED DESCRIPTION

Figures 2A, 2B, 2C:
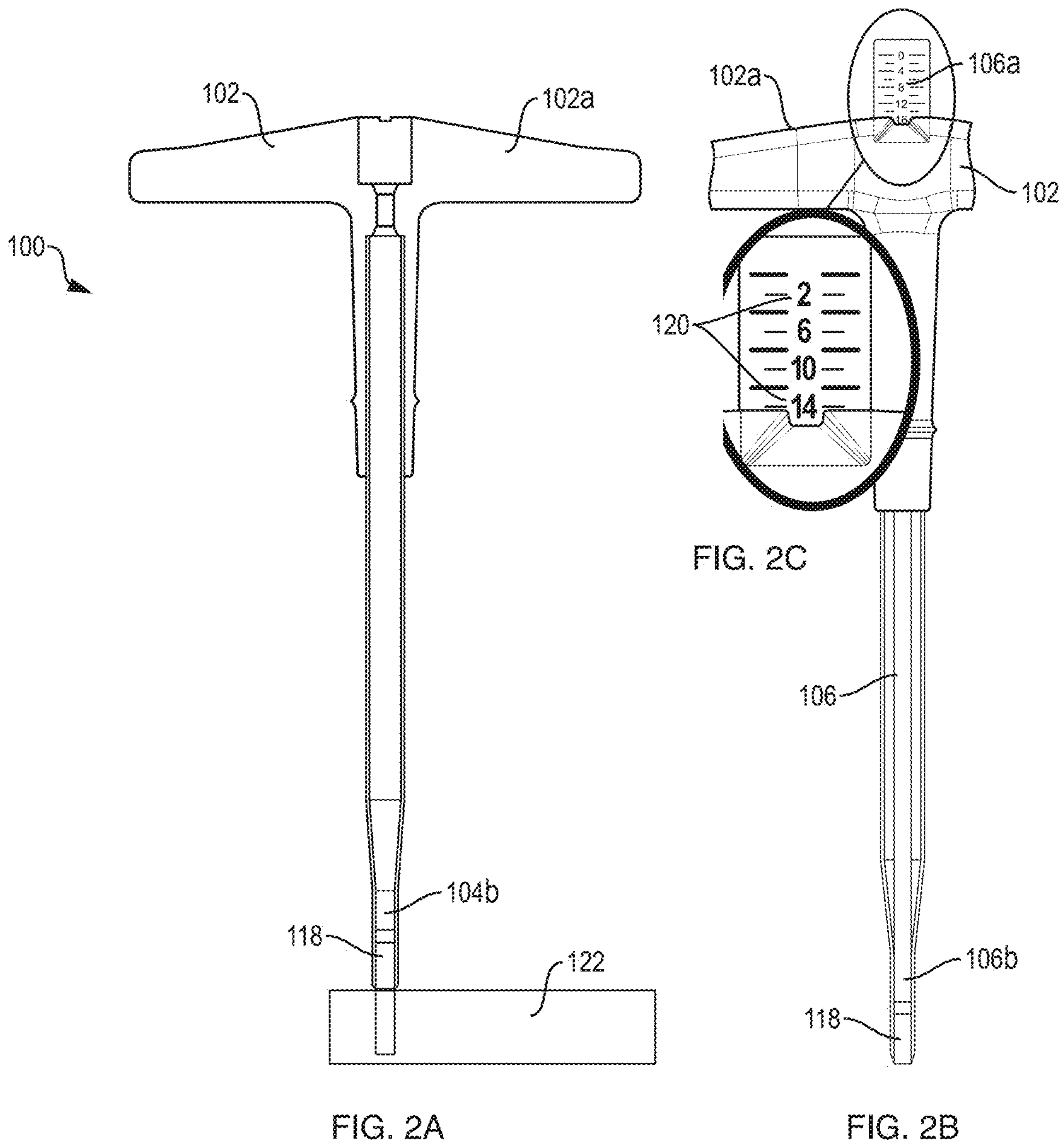
FIGS. 2A-C illustrate an example of a method of harvesting a tissue graft of this disclosure using the tissue transfer device of FIG. 1A.

In the following description, like components have the same reference numerals, regardless of different illustrated examples. To illustrate examples clearly and concisely, the drawings may not necessarily reflect appropriate scale and may have certain features shown in somewhat schematic form. The disclosure may describe and/or illustrate features in one example, and in the same way or in a similar way in one or more other examples, and/or combined with or instead of the features of the other examples.

In the specification and claims, for the purposes of describing and defining the invention, the terms "about" and "substantially" represent the inherent degree of uncertainty attributed to any quantitative comparison, value, measurement, or other representation. The terms "about" and "substantially" moreover represent the degree by which a quantitative representation may vary from a stated reference without resulting in a change in the basic function of the subject matter at issue. Open-ended terms, such as "comprise," "include," and/or plural forms of each, include the listed parts and can include additional parts not listed, while terms such as "and/or" include one or more of the listed parts and combinations of the listed parts.

FIG. 1A shows an example of a tissue transfer device 100 of this disclosure. In examples, the device 100 may generally comprise a handle 101, a chisel in the form of an outer tube 104 coupled to the handle 101, an inner shaft 106 disposed within the outer tube 104, and a control mechanism, such as a lever arm 108, removeably coupled to the handle 101 to expel a tissue graft in a controlled manner. In examples, the lever arm 108 may rotate about a pivot 114 in a housing 116 to contact the inner shaft 106. In examples, the handle 101 may have a "T" shape with an elongated first portion 102 having a first surface 102*a* and a second surface 102*b* opposite the first surface 102*a*. A second portion 103 may extend perpendicular to the first portion 101 from an approximate center of the second surface 102*b*. A through hole 110 defined by the handle 101 may extend through a width of the first portion 102 and through the second portion 103. The outer tube 104 may have a proximal end 104*a* coupled to the second portion 103 of the handle 101 and a distal end 104*b* configured for insertion into tissue. A cannulation 112 defined by the outer tube 104 may extend between the proximal and distal ends 104*a,b* of the outer tube 104 such that the cannulation 112 may extend in line with the through hole 110. The disclosure also contemplates other shapes and configurations of the handle 101 where the cannulation 112 of the outer tube 104 may extend in line with a through hole 110 defined by the handle 101.

As shown in FIG. 1B, the inner shaft 106 may extend through the cannulation 112 of the outer tube 104 such that a proximal end 106*a* of the inner shaft 106 can project from the first surface 102*a* of the handle 101. The inner shaft 106 may be both axially moveable relative to and removeable from the outer tube 104. A diameter of the proximal end 106*a* may be selected to be wider than an inner diameter of the cannulation 112 such that, when the inner shaft 106 is fully inserted into the outer tube 104, the proximal end 106*a* contacts the first surface 102*a* of the handle 101. Contact with the lever arm 108 (FIG. 1A) may move the inner shaft 106 distally relative to the outer tube 104 to expel a tissue graft 118 from the outer tube 104. Thus, the lever arm 108 advantageously provides a controlled mechanism for expelling the tissue graft 118. In other examples, not shown, the lever arm 108 can include a cam or four bar mechanism to vary the mechanical advantage as a function of the position of the lever arm 108. The disclosure also contemplates other suitable leverage magnifying mechanisms of the lever arm 108.

FIG. 1C shows a detailed view of the proximal end 106*a* of the inner shaft 106. In examples, the proximal end 106*a* may comprise laser marks or indicia 120 corresponding to a desired length of the tissue graft 118. Thus, the surgeon can use the indicia 120 to measure the length of the tissue graft 118 before harvesting. The first surface 102*a* of the handle 101 may furthermore include a notched area 121 for easier visualization of the indicia 120.

FIGS. 2A-C illustrate an example of a method of harvesting a tissue graft 118 of this disclosure using the tissue transfer device 100 of FIGS. 1A-C. As shown in FIG. 2A, with the inner shaft 106 removed from the tissue transfer device 100, the user may initially insert the distal end 104*b* of the outer tube 104 into healthy cartilage tissue 122 (for example, by malleting the first surface 102*a* of the handle 101). In examples, the cartilage tissue 122 may comprise the patient's own tissue (i.e., an "autograft"). However, the disclosure also contemplates that the cartilage tissue can come from a donor (i.e., an "allograft"). Malleting the handle 101 forces the tissue graft 118 to enter the distal end 104*b* of the outer tube 104. The user may then remove the device 100 from the tissue 122 with the tissue graft 118 disposed inside the distal end 104*b*. As shown in FIG. 2B, the user then may insert the inner shaft 106 into the outer tube 104 such that a distal end 106*b* of the inner shaft 106 contacts the tissue graft 118. Thus, the proximal end 106*a* of the inner shaft 106 may project from the first surface 102*a* of the handle 101. As shown in FIG. 2C, the indicia 120 may allow the user to determine a length of the tissue graft 118.

In alternative methods, not shown, if the user desires to create a tissue graft 118 having a specific length, the user could first adjust the placement of the inner shaft 106 within the outer tube 104, and then mallet the outer tube 104 into the tissue 122 to create the tissue graft 118 having the specified length. Alternatively, the user can harvest the graft 118 to a length in excess of the desired length and, using the indicia 120, push the graft 118 out of the outer tube 104 until the desired length of the graft 118 is achieved. The user can then cut off the excess portion of the graft 118, leaving the desired length graft in the tube.

Figures 3A, 3B, 3C, 3D:
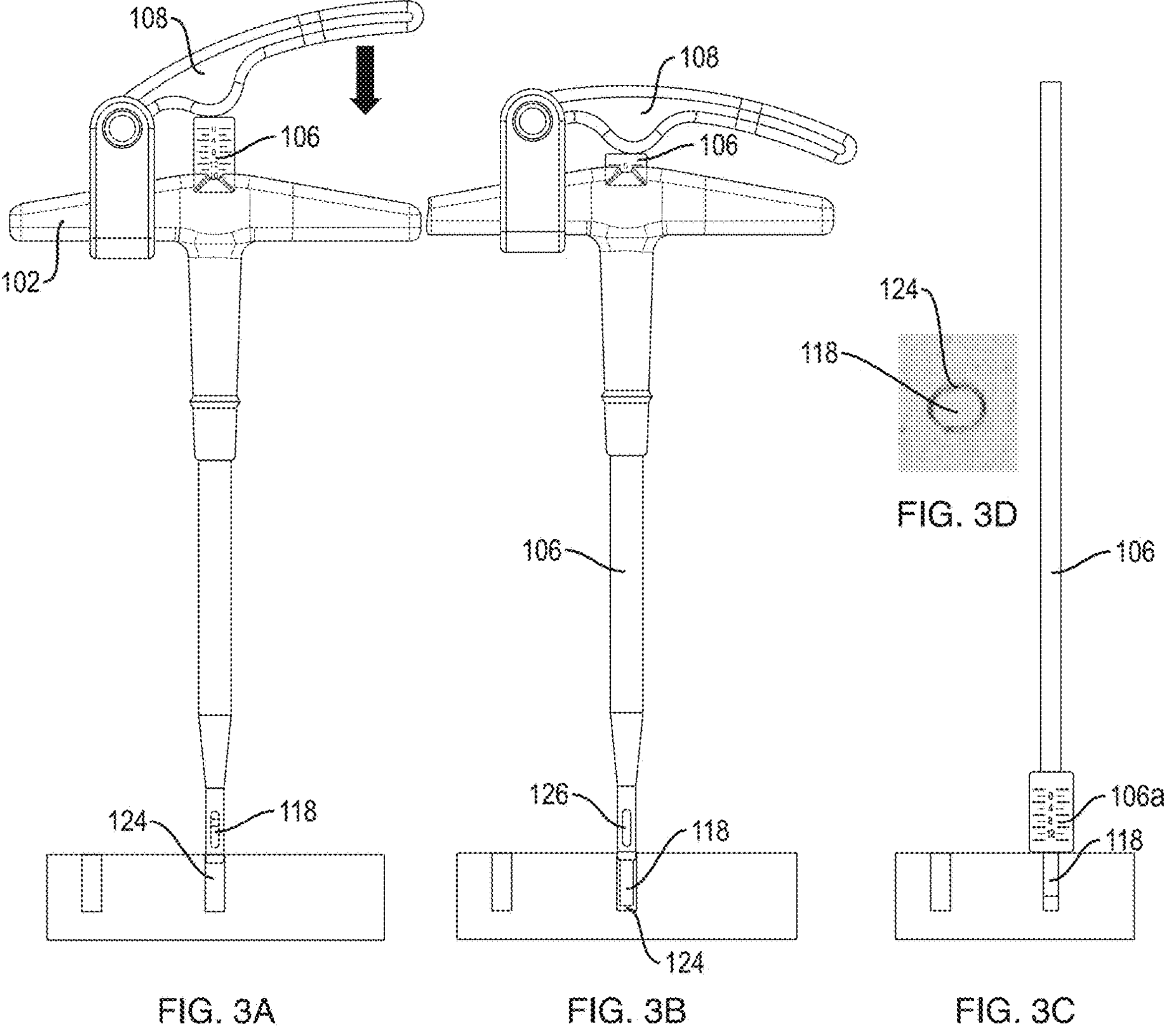
FIGS. 3A-D illustrate an example of a method of tissue repair using the tissue transfer device of FIG. 1A.

FIGS. 3A-F illustrate a method of tissue repair using the harvested tissue graft 118. As shown in FIG. 3A, the user may first create a hole 124 in the area of the defect to a depth selected to be equal to a length of the tissue graft 118. The user can create the hole 124 by any means known in the art. In cases where the lever arm 108 may be not preassembled to the handle 101, the user can also assemble the lever arm 108 to the handle 101. As shown in FIG. 3B, with the inner shaft 106 and the tissue graft 118 disposed inside the outer tube 104, the user may then actuate the lever arm 108 such that the lever arm 108 causes the inner shaft 106 to move distally to expel the tissue graft 118 into the hole 124. In examples, a window 126 defined in an outer surface of the outer tube 104 allows for direct visualization of the expulsion of the tissue graft 118. Advantageously, as shown in FIG. 3C, the user can then remove the inner shaft 106 from the device 100 and use the proximal end 106*a* to tamp the tissue graft 118 flush with the hole 124. As such, the tissue graft 118 neatly conforms to the hole 124, as shown in FIG. 3D.

Figures 4A, 4B, 4C:
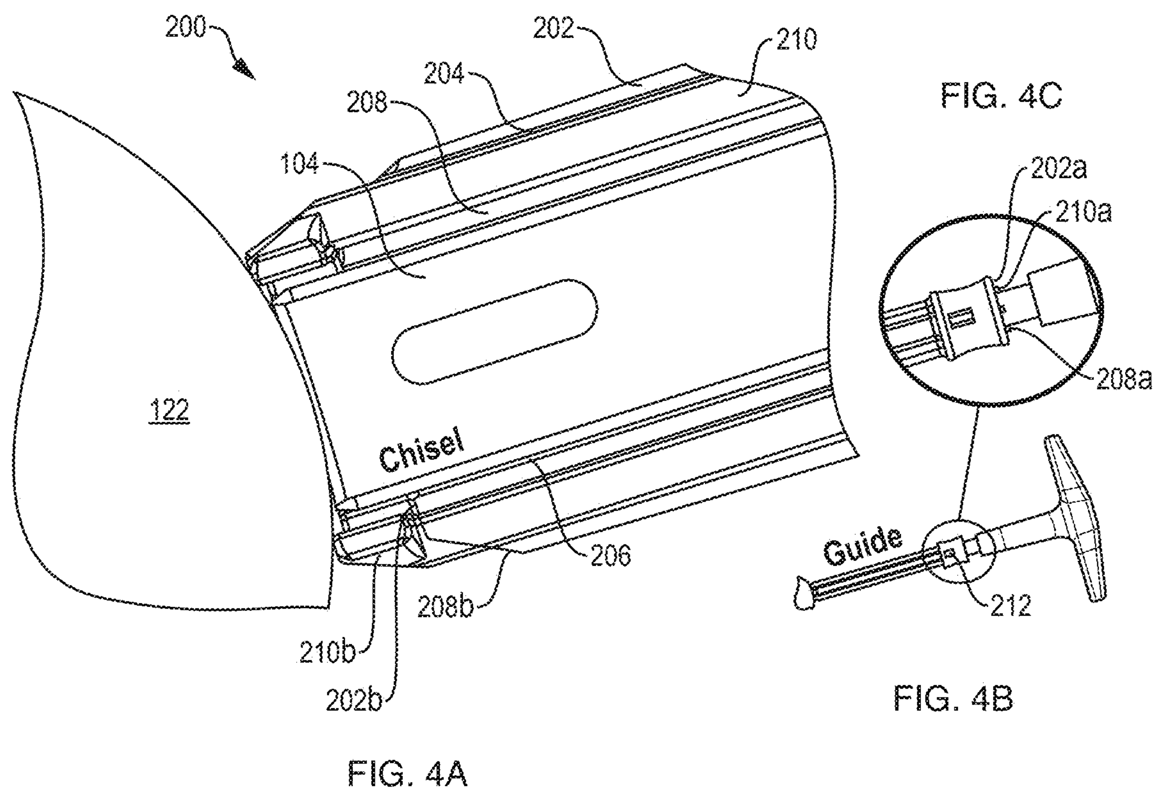
FIGS. 4A-C illustrate an example of an alignment guide for use with the tissue transfer device of FIG. 1A.

FIGS. 4A-C illustrate an example of an alignment guide 200 for optional use with a tissue transfer device, such as the tissue transfer device 100, 700. In examples, the guide 200 may be formed integrally with or attached to the tissue transfer device 100. As shown in the cross-sectional view of FIG. 4A, the guide 200 may have a substantially cylindrical, elongated body 202 comprising a beveled distal surface 202*b* and a proximal surface 202*a*. An outer wall 204 may define a central cannulation 206 extending between the distal surface 202*b* and the proximal surface 202*a*. The cannulation 206 may be configured to receiving the outer tube 104 of the tissue transfer device 100. The outer wall 204 may further defines a plurality of linear channels 208 spaced equidistant from one another about a circumference of the body 202. In examples, the plurality of channels 208 may be four channels 208 spaced 90° apart about a circumference of the body 202. However, the disclosure contemplates more or fewer than four channels 208. Each of the channels 208 may be configured for the passage of a sliding pin 210. A distal end 210*b* of the pins 210 may be configured to extend from a distal opening 208*b* of the channels 208 to contact the tissue 122. As shown in FIG. 4B, in examples, the body 202 may define one or more windows 212 for direct visualization of the pins 210. As shown in FIG. 4C, a length of the pins 210 may be selected to be longer than a length of the linear channels 208 such that a proximal end 210*a* of the pins 210 can also project from proximal openings 208*a* of the channels 208 when the pins 210 contact the tissue 122. The proximal ends 210*a* of the pins 210 may serve as a visual indicator to the user, as further described below.

Figures 4D, 4E:
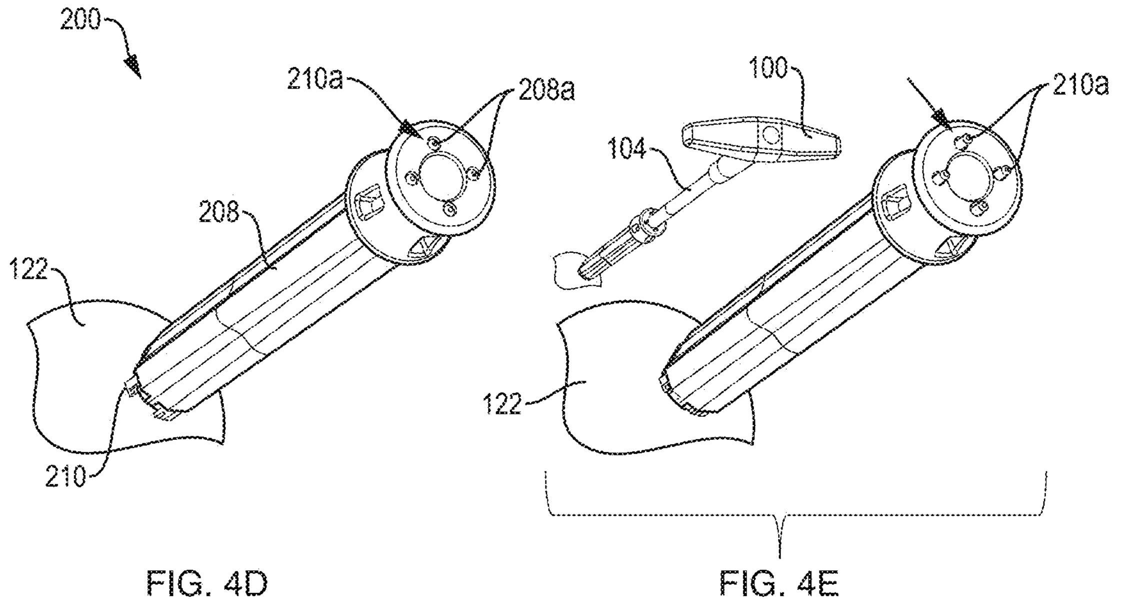
FIGS. 4D and 4E show examples of the guide of FIGS. 4A-C when the tissue transfer device is in a misaligned position (FIG. 4D) and an aligned position (FIG. 4E)

FIGS. 4D and 4E show perspective views of the guide 200 when the tissue transfer device 100 is in a misaligned position (FIG. 4D) and in an aligned position (FIG. 4E). As shown in FIG. 4D, when the outer tube 104 is not perpendicular to the tissue 122 (for example, when part of the outer tube 104 contacts an area of the tissue 122 that sits proud of a surrounding area), the proximal ends 210*a* of the pins 210 do not project from the proximal openings 208*a*. This alerts the user that the outer tube 104 is not perpendicular to the tissue 122. In contrast, as shown in FIG. 4E, when the outer tube 104 is perpendicular to the tissue 122 (that is, when all parts of the outer tube 104 are in equal contact with the tissue 122), all of the proximal ends 210*a* of the pins 210 project equally from the proximal openings 208*a*. The proximal ends 210*a* of the pins 210 thus visually indicate to the user that the outer tube 104 is perpendicular to the tissue. The disclosure also contemplates that, in some cases (not shown), when only part of the outer tube 104 contacts the tissue 122, one or more pins 210 also contact the tissue 122 while the other pins 210 do not. Therefore, only some of the proximal ends 210*a* of the pins 210 project from the proximal openings 208*a*, alerting the user that the outer tube 104 may be less than fully perpendicular to the tissue 122.

Figure 5A:
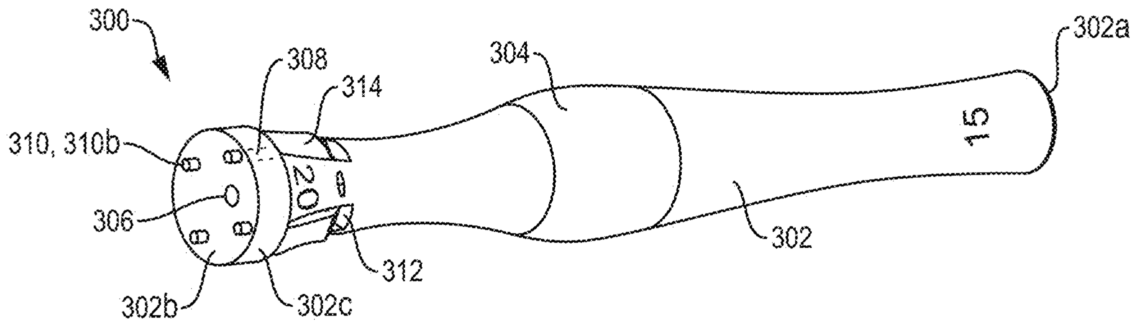
FIGS. 5A and 5B illustrate another example of an alignment guide for use with a guidewire of this disclosure.
Figure 5B:
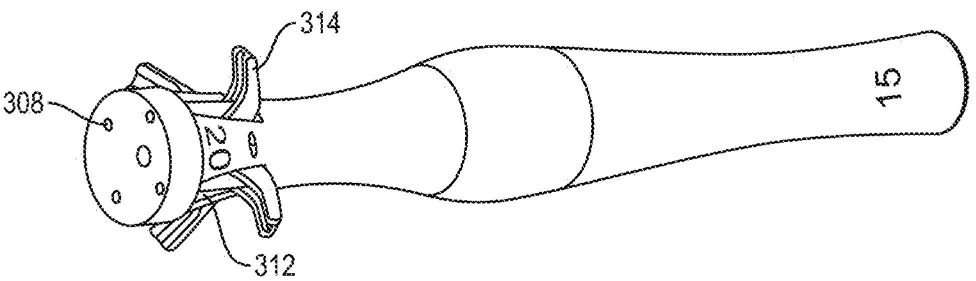

FIGS. 5A and 5B illustrate another example of an alignment guide 300 for optional use with a guidewire (not shown). In examples, the guide 300 may be formed integrally with or attached to the guidewire. As shown in FIG. 5A, the guide 300 may have a substantially cylindrical, elongated body 302 comprising a distal surface 302*b* and a proximal surface 302*a*. An outer wall 304 may define a central cannulation 306 extending between the distal surface 302*b* and the proximal surface 302*a* for receiving the guidewire. The outer wall 304 at a distal end 302*c* of the body 300 may defines a plurality of channels 308 spaced equidistant from one another about a circumference of the body 302. In examples, the plurality of channels 308 may be four channels 308 spaced 90° apart about a circumference of the body 302. However, the disclosure contemplates more or fewer than four channels 308. Each channel 308 may be configured for the passage of a sliding pin 310. A distal end 310*b* of the sliding pins 310 may be configured to extend from the distal surface 302*b* of the body 302 to contact tissue. Furthermore, each of the plurality of pins 310 may operatively couple to a fin 314 deployable through a window 312 defined by the outer wall 304 at the distal end 302*c* of the body 302. As shown in FIG. 5B, the fins 314 are configured to deploy from the window 312 (for example, by pivoting outward) when the pins 310 contact the tissue 122. Thus, the fins 314 may serve as a visual indicator to the user, as further described below.

Figures 5C, 5D, 5E:
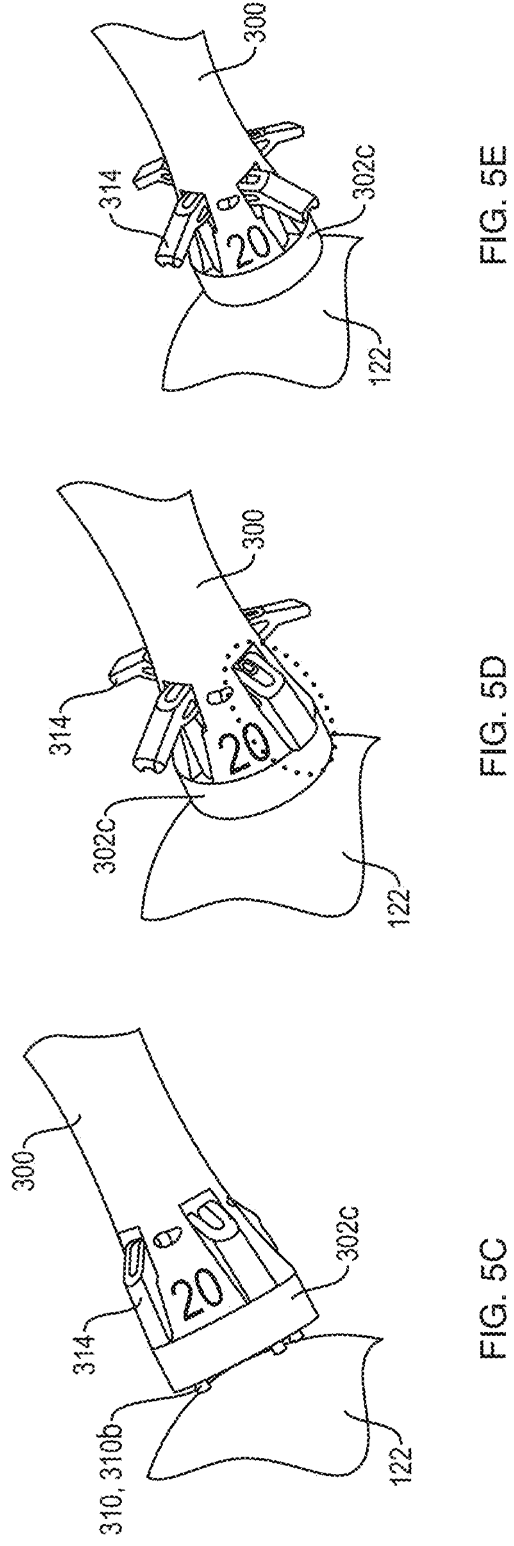
FIGS. 5C-E show examples of the guide of FIGS. 5A and 5B in a misaligned position (FIG. 5C), a partially aligned position (FIG. 5D), and an aligned position (FIG. 5E)

FIGS. 5C-E show the guide 300 in a misaligned position (FIG. 5C), a partially aligned position (FIG. 5D), and an aligned position (FIG. 5E). As shown in FIG. 5C, when the guide 300 is not perpendicular to the tissue 122 (for example, when the distal end 302*b* of the guide 300 contacts an area of the tissue 122 that sits proud of a surrounding area), the distal ends 310*b* of the pins 310 do not contact the tissue 122. In this case, the fins 314 do not deploy, alerting the user that the guide 300 is not perpendicular to the tissue 122 and the guidewire therefore may be misaligned. As shown in FIG. 5D, in some cases, when only part of the distal end 302*b* of the guide 300 contacts the tissue 122, one or more of the distal ends 310*b* of the pins 310 also contact the tissue 122 while other distal ends 310*b* of the pins 310 do not. Therefore, not all of the fins 314 deploy, alerting the user that the guide 300 is not perpendicular to the tissue 122 and the guidewire may be only partially aligned. Finally, as shown in FIG. 5E, when the distal end 302*b* of the guide 300 fully contacts the tissue 122, all of the distal ends 310*b* of the pins 310 also contact the tissue 122. Therefore, all of the fins 314 deploy, alerting the user that the guide 300 is perpendicular to the tissue 122 and the guidewire is fully aligned.

With regard to the guides 200, 300 described above, the disclosure also contemplates other indicator mechanisms, such as LED lights that separately activate when a pin 210, 310 contacts the tissue 122. The disclosure also contemplates that the guides 200, 300 could include mechanisms to provide tactile indications to the user, or compliant indicator mechanisms. Moreover, in cases where the user desires to perform a cartilage repair at a specific non-perpendicular angle, the disclosure contemplates that a configuration of the guides 200, 300 could indicate proper alignment at the selected angle.

Figures 6A, 6B, 6C:
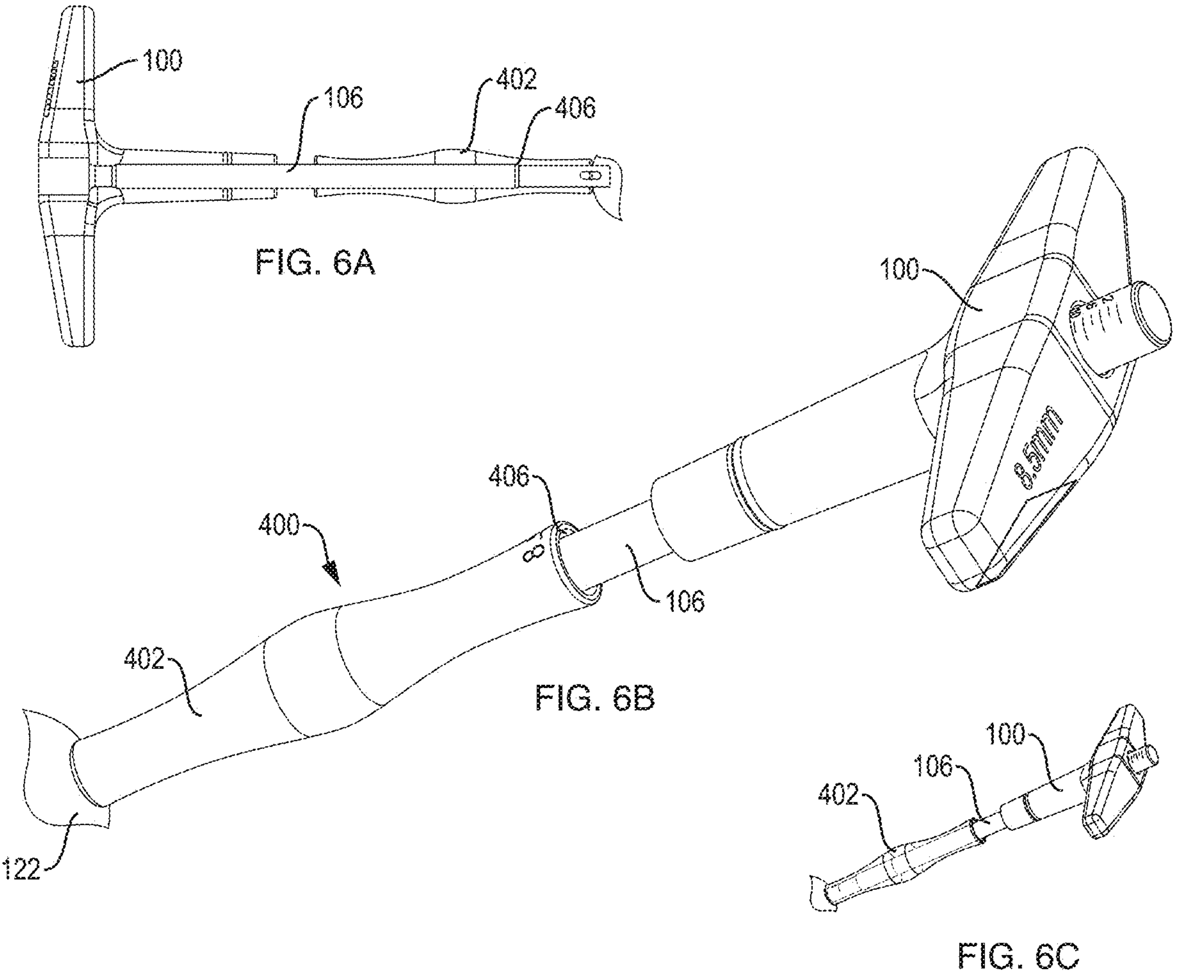
FIGS. 6A-C illustrate another example of an alignment guide for use with the tissue transfer device FIG. 1A.

FIGS. 6A-C show another example of a guide 400 configured for use with the tissue transfer device 100 of FIGS. 1A and 1B. As shown in FIGS. 6A-C, the body 402 of the guide 400 defines a central cannulation 406 for receiving the outer tube 104 of the tissue transfer device 100. The guide 400 relies on distal surface contact with the tissue 122, and without the indicators as described above with regard to guides 200 and 300. Advantageously, the guide 400 is therefore simpler and less expensive to manufacture than guides 200 and 300.

Figure 7A:
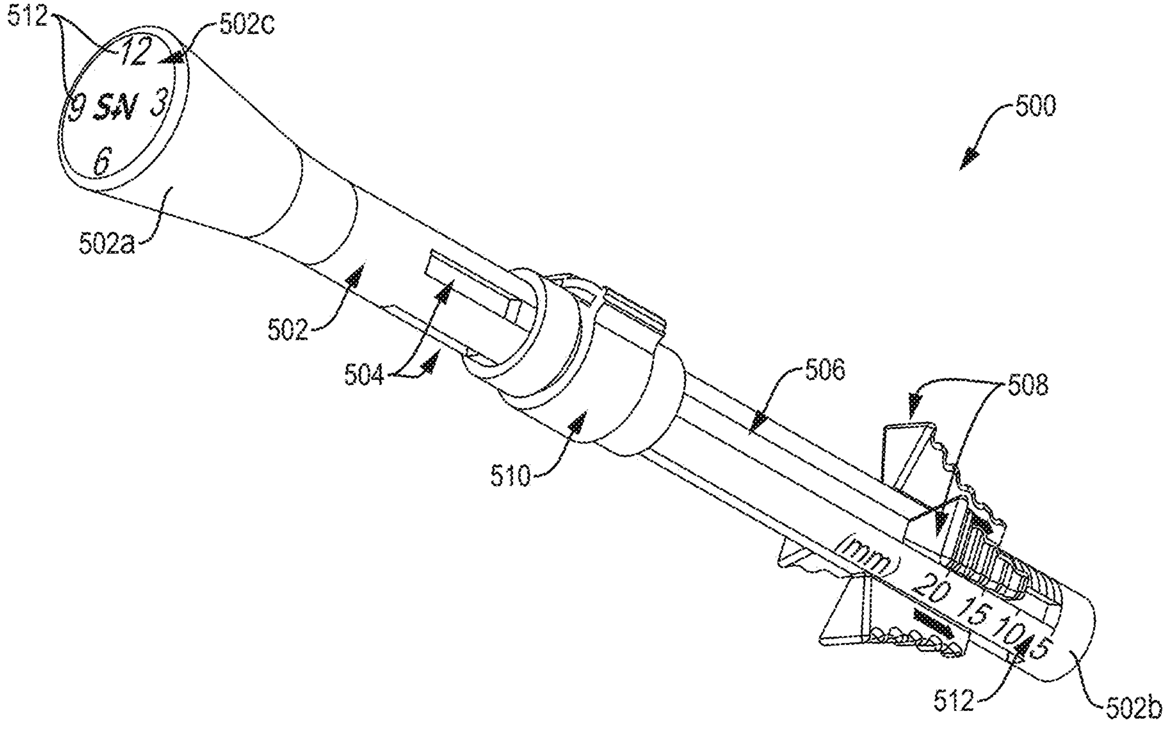
FIG. 7A shows an example of a depth measurement tool for measuring a depth of a hole in a defect area of tissue.

FIG. 7A shows an example of a depth measurement tool 500 for measuring a depth of a hole 124 in a defect area of tissue 122 (FIG. 3A). As shown in FIG. 7A, the tool 500 may comprise a substantially cylindrical, elongated body 502 having a proximal end 502*a* and a distal end 502*b*. An outer surface of the body 502 defines a plurality of grooves 504 spaced equidistant from one another about a circumference of the body 502. In examples, the plurality of grooves 504 may be four grooves 504 spaced 90° apart about a circumference of the body 502. However, the disclosure contemplates more or fewer than four grooves 504. Each groove 504 houses a sliding bar 506 that can freely slide inside the groove 504. Each sliding bar 506 may include a finger-engageable handle 508 to facilitate sliding the bars 506. A releasable locking mechanism 510, such as a clamp, may lock the sliding bars 506 in their desired positions. The proximal end 502*a* of the body 502 may also include indicia 512 to indicate a depth of the hole 124. A proximal face 502*c* may include further indicia 512, such as a clock face, to help the user orient the tool 500 relative to an anatomical reference on the tissue 122.

Figures 7B, 7C:
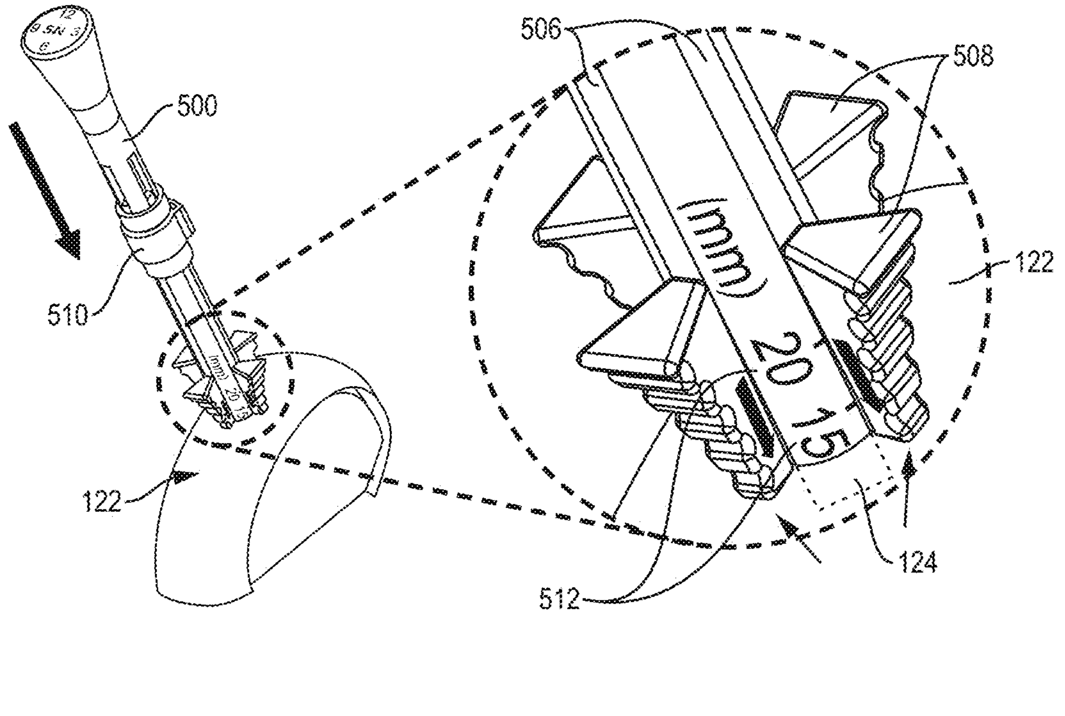
FIGS. 7B and 7C illustrate examples of using the tool FIG. 7A to measure the depth of the hole.

FIGS. 7B and 7C illustrate an example of using the tool 500 of FIG. 7A to measure the depth of the hole 124. As shown in FIGS. 7B and 7C, in examples, the user may fully insert the tool 500 into the hole 124. Using the handles 508, the user may then individually push each sliding bar 506 such that each handle 508 contacts the surface of the tissue 122. The user may activate the locking mechanism 510 to hold the bars 506 in place. The user may then remove the tool 500 from the hole 124 and determines the distance from the bottom of the hole 124 to the surface of the tissue 122 from the indicia 512 next to each bar 506. Advantageously, the tool allows the user to determine a depth of the hole 124 at a plurality of different locations about the hole 124 substantially simultaneously.

Figure 8:
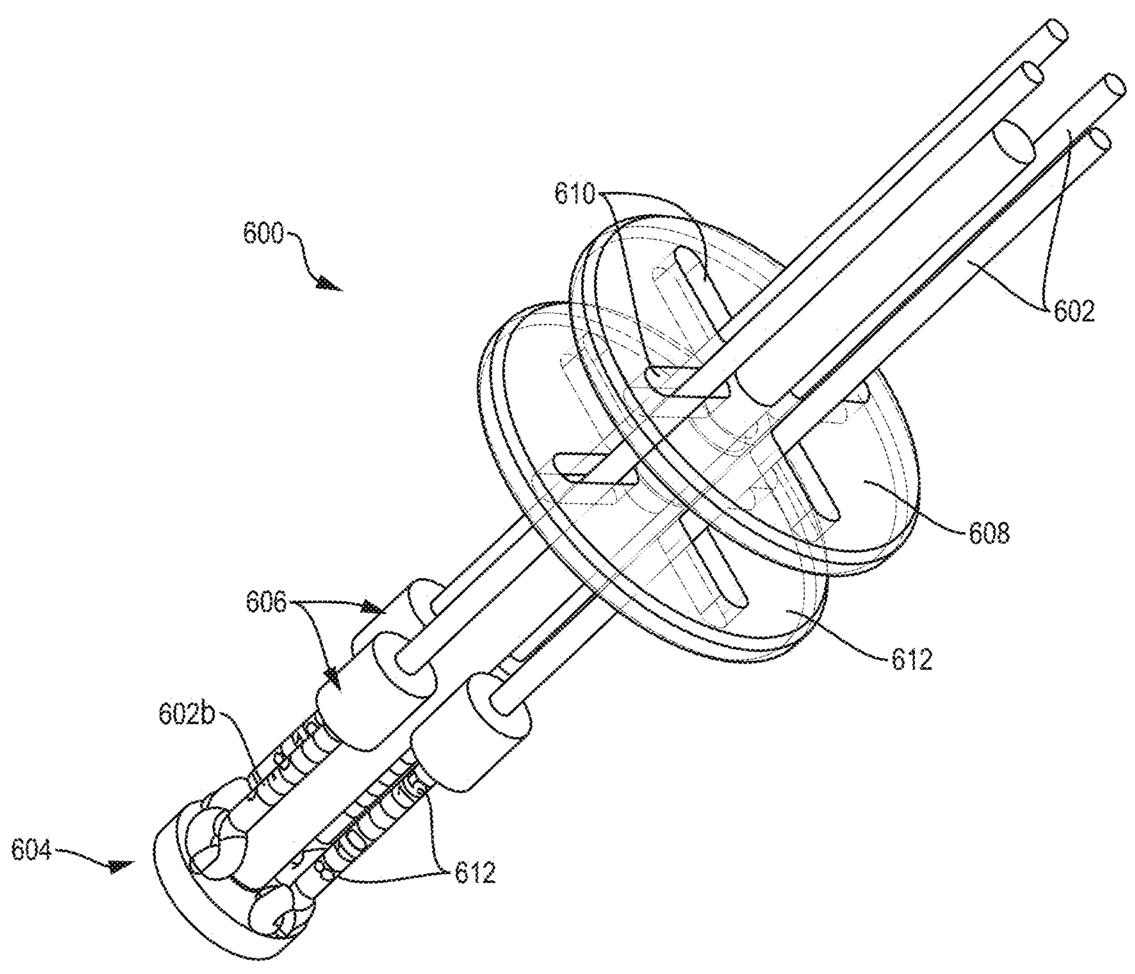
FIG. 8 shows another example of a depth measurement tool for measuring a depth of a hole in a defect area of tissue.

FIG. 8 shows another example of a depth measurement tool 600 for measuring a depth of a hole 124 in a defect area of tissue. The tool 600 may comprise a plurality of bars 602 attach to a ring member 604 or other flat, circular element. In examples, the tool 600 may include four bars 602, as shown. However, the disclosure contemplates more or fewer than four bars 602. The bars 602 may extend through slots 610 of a guide member 608. The slots 610 may be configured to manage the orientation of the bars 602 and ensure the bars 602 maintain perpendicular planes. The slots 610 may extend longitudinally toward an outer perimeter 612 of the guide member 608 to allow adjustment of the bars 602 based on an outer size of the hole 124. The distal end 602*b* of the bars 602 may also include indicia 612 to indicate a depth of the hole 124. The ring member 604 may be configured to engage the bottom of the hole 124. The user can then independently push down a sliding member 606 (for example, a sliding rubber washer) on each bar 602 to contact the surface of the tissue 122. In examples, friction between the sliding members 606 and the bars 602 may hold the sliding members 606 in place. The user may then remove the tool 600 from the hole 124 and determine the distance from the bottom of the hole 124 to the surface of the tissue 122 from the indicia 612 on each bar 602. In other examples of the tool 600 (not shown), the holding mechanism can include clamps, a ratchet mechanism, screws or knobs. Advantageously, the tool 600 allows the user to determine a depth of the hole 124 at a plurality of different locations about the hole 124 substantially simultaneously.

Figure 9A:
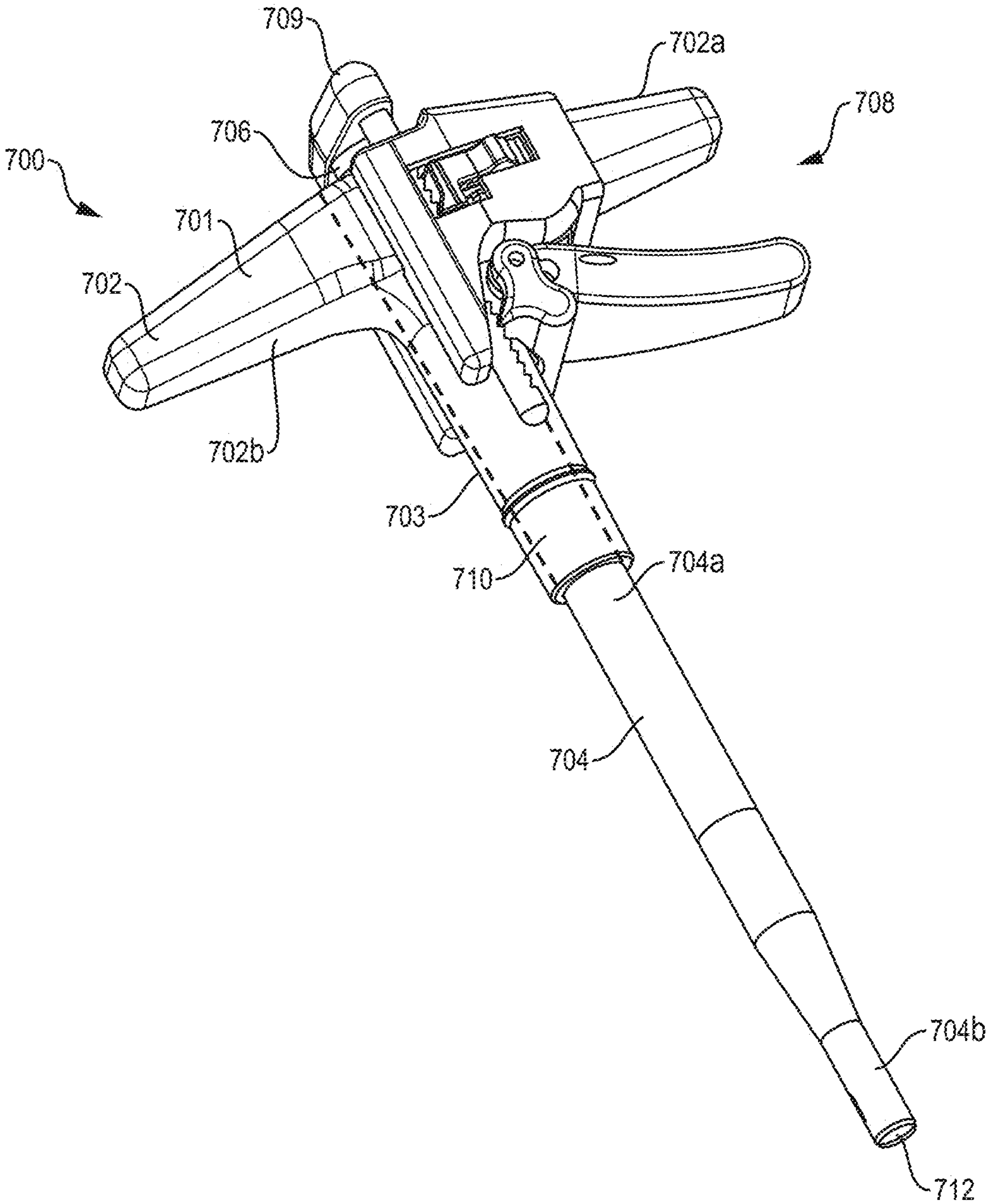
FIG. 9A-C illustrate another example of the tissue transfer device of this disclosure.

FIG. 9A shows another example of a tissue transfer device 700 of this disclosure. The device 700 may be substantially similar to the device 100 in design and use, except as described below. In examples, the device 700 may generally comprise a handle 701, a chisel in the form of an outer tube 704 coupled to the handle 701, an inner shaft 706 disposed within the outer tube 704, and a control mechanism, such as a ratchet mechanism 708, removeably coupled to the handle 701 to expel a tissue graft in a controlled manner. In examples, the handle 701 may have a "T" shape with an elongated first portion 702 having a first surface 702*a* and a second surface 702*b* opposite the first surface 702*a*. A second portion 703 may extend perpendicular to the first portion 702 from an approximate center of the second surface 702*b*. A through hole 710 defined by the handle 701 may extend through a width of the first portion 702 and through the second portion 703. The outer tube 704 may have a proximal end 704*a* coupled to the second portion 703 of the handle 701 and a distal end 704*b* configured for insertion into tissue. A cannulation 712 defined by the outer tube 704 may extend between the proximal and distal ends 704*a,b* of the outer tube 704 such that the cannulation 712 may extend in line with the through hole 710. The disclosure also contemplates other shapes and configurations of the handle 701 where the cannulation 712 of the outer tube 704 may extend in line with a through hole 710 defined by the handle 701.

Figure 9B:
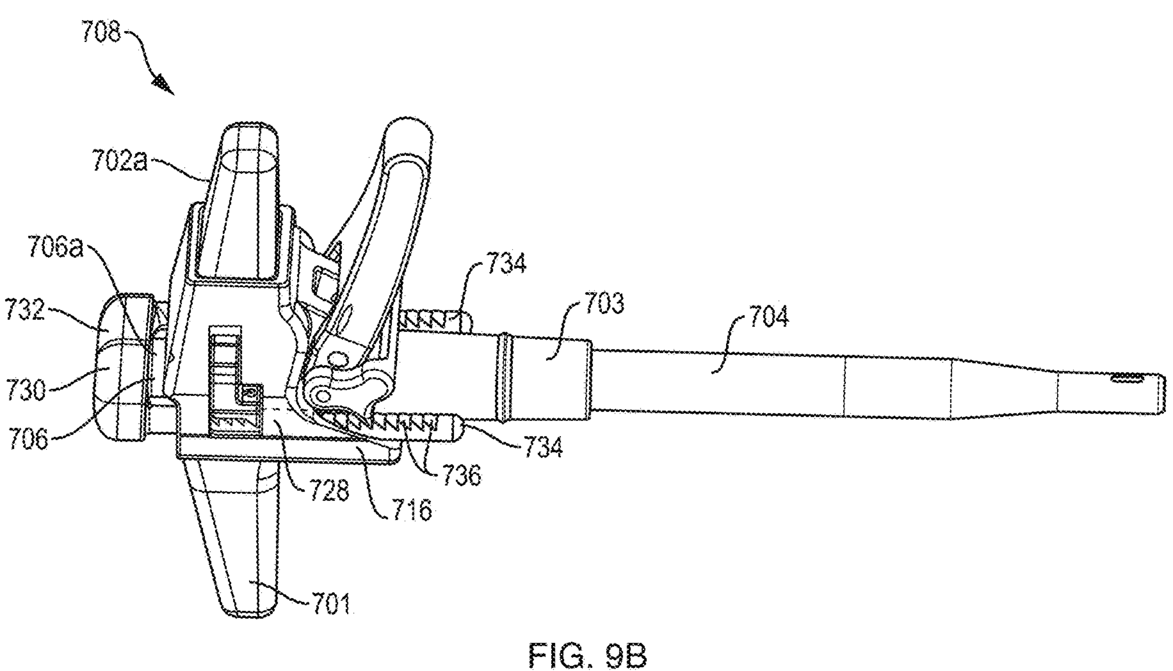
Figure 9C:
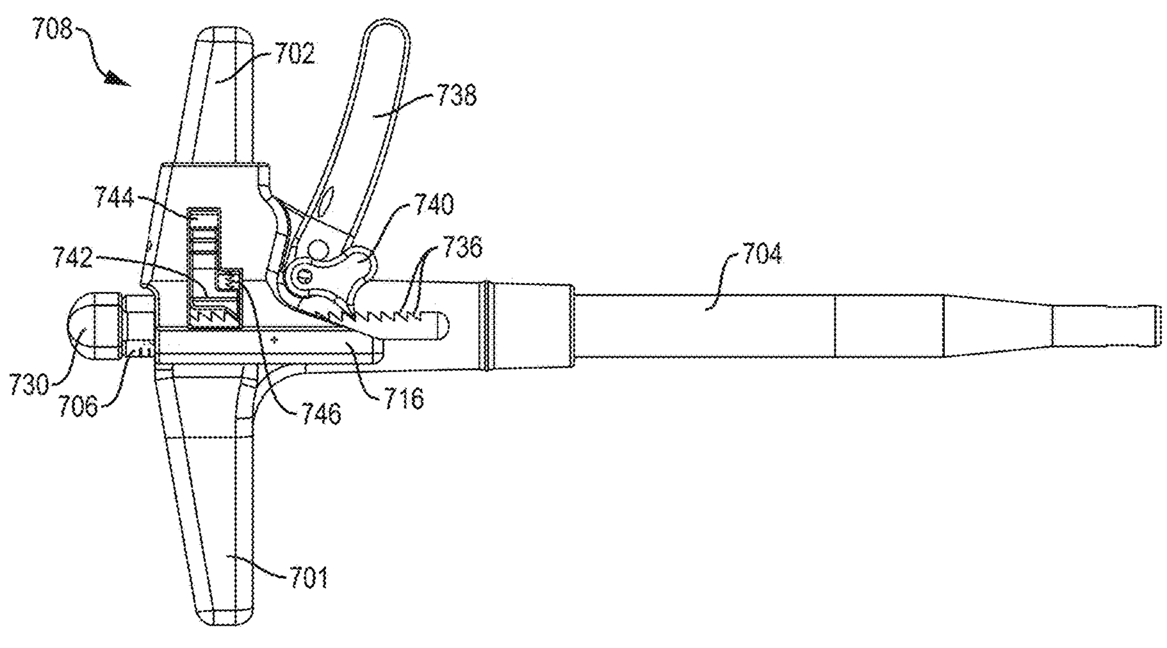

FIGS. 9B and 9C show the device 700 in a perspective view (FIG. 9B) and a side view (FIG. 9C). As shown in FIG. 9B, the inner shaft 706 may extend through the outer tube 704 such that a proximal end 706*a* of the inner shaft 706 projects from the first surface 702*a* of the handle 701. Examples of the ratchet mechanism 708 may include a ratchet body 716 removeably coupled to the handle 701. The ratchet body 716 may define slots 728 extending through the ratchet body 716 on opposing sides of the second portion 703. A plunger 730 may include a transverse portion 732 in contact with the proximal end 706*a* of the inner shaft 706, and two arm portions 734 extending through a respective one of the slots 728. An outer surface of the arm portions 734 may further define a plurality of teeth 736. As shown in FIG. 9C, a lever 738 may pivotably couple to the ratchet body 716. A ratchet pawl 740 may further couple to the lever 738 and be configured to serially engage one of the plurality of teeth 736 when the lever 738 is actuated toward the first portion 702 of the handle 701. Thus, serial engagement of the ratchet pawl 740 with the plurality of teeth 736 may move the inner shaft 706 distally relative to the outer tube 704 to expel a tissue graft from the outer tube 704. In examples, the ratchet mechanism 708 may further include a locking pawl 742 for locking the plunger 730 at a desired position relative to the ratchet body 716. In examples, the ratchet body 716 may include a window 744 for accessing the locking pawl 742, which may be biased by at least one spring 746 toward the arms 734 to maintain the locking pawl 742 in the locked position. The ratchet mechanism 708 advantageously increases the mechanical advantage of the device 700 while also greatly increasing the deployment control of the graft. For example, each motion cycle of the lever 738 can push the graft a specified distance (e.g. 2 mm), giving the user better control during the deployment of the graft.

Figures 10A, 10B:
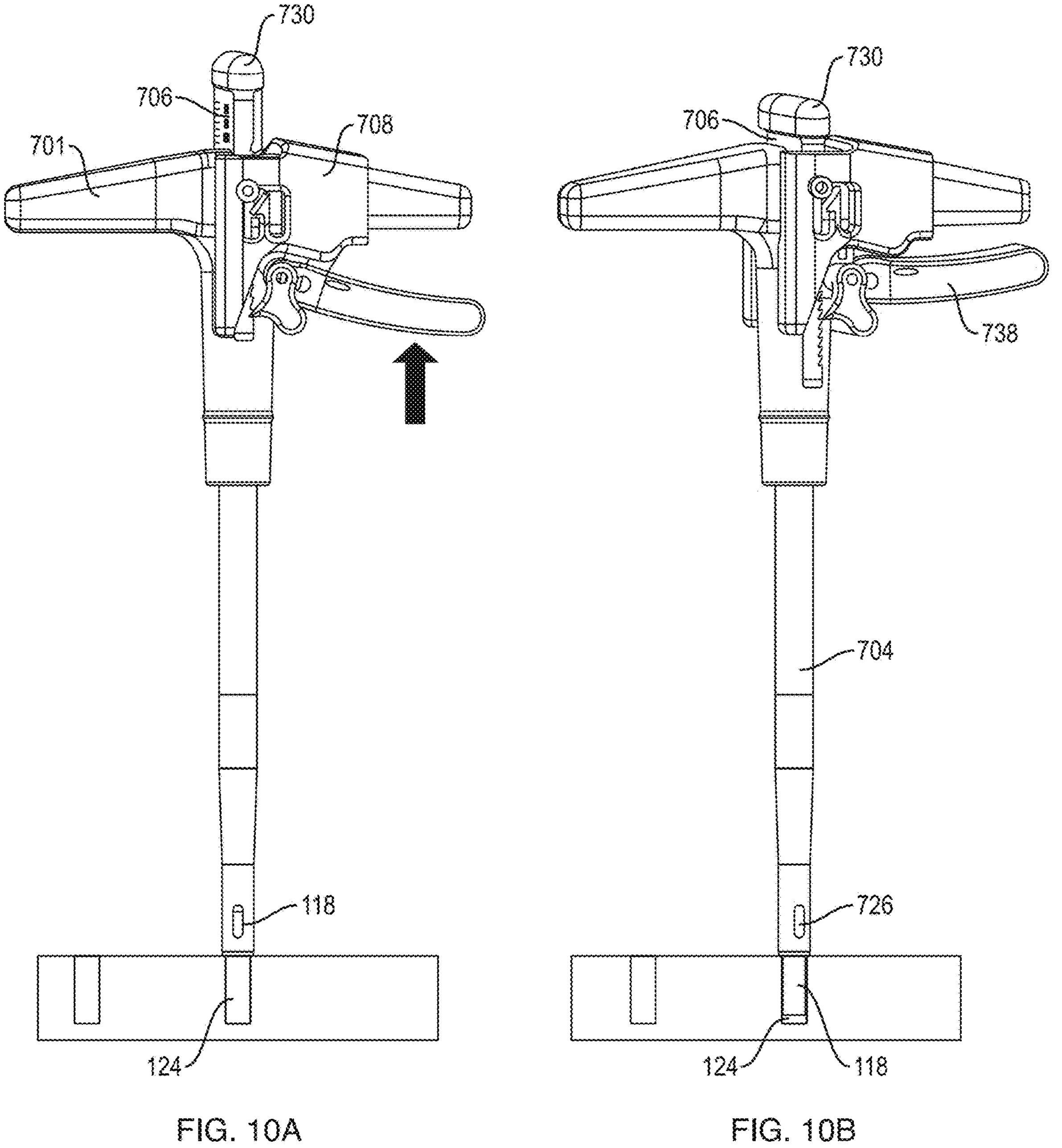
FIGS. 10A-D illustrate a method of tissue repair using the tissue transfer device of FIGS. 9A-C.
Figures 10C, 10D:
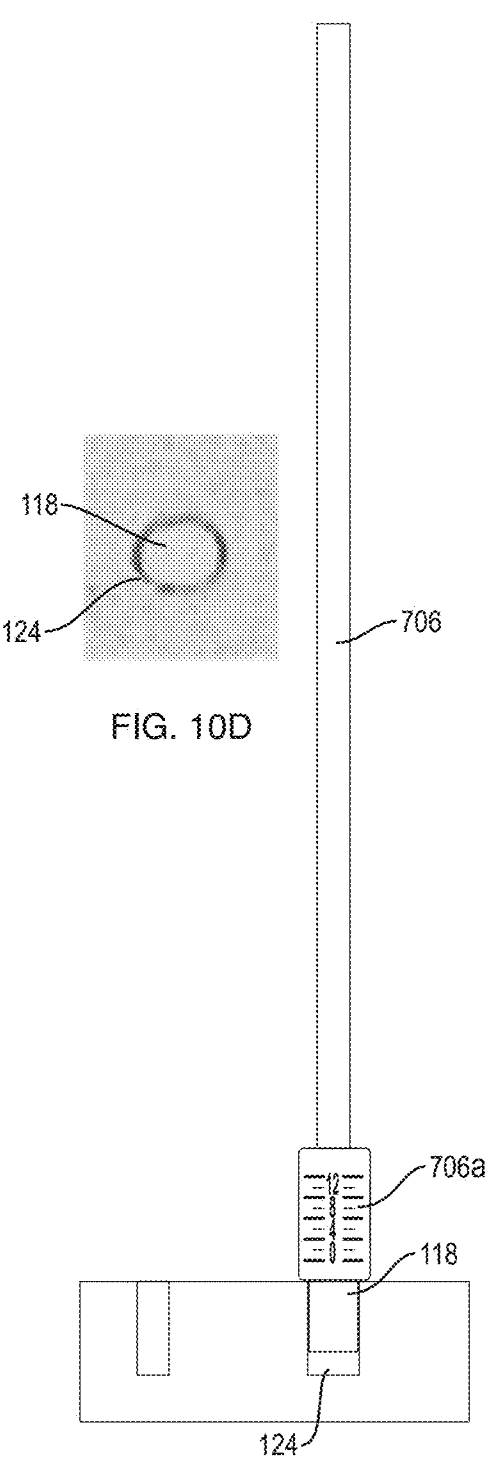

FIGS. 10A-D illustrate a method of tissue repair using a harvested tissue graft 118. The tissue graft 118 may be harvested with the device 700 in a similar manner to that illustrated in FIGS. 2A-C (that is, by malleting the device 700 into an area of healthy tissue such that the tissue graft 118 is forced to enter the distal end 704*b* of the outer tube 704). As shown in FIG. 10A, the user may first create a hole 124 in the area of the defect to a depth selected to be equal to a length of the tissue graft 118. In cases where the ratchet mechanism 708 may be not preassembled to the handle 701, the user can also assemble the ratchet mechanism 708 to the handle 701. As shown in FIG. 10B, with the inner shaft 706 and the tissue graft 118 disposed inside the outer tube 704, the user may then actuate the lever 738 to cause distal movement of the plunger 730, which in turn causes the inner shaft 706 to move distally to expel the tissue graft 118 into the hole 124. In examples, a window 726 defined in an outer surface of the outer tube 704 allows for direct visualization of the expulsion of the tissue graft 118. Advantageously, as shown in FIG. 10C, the user can then remove the inner shaft 706 from the device 700 and use the proximal end 706*a* to tamp the tissue graft 118 flush with the hole 124. As such, the tissue graft 118 neatly conforms to the hole 124, as shown in FIG. 10D.

FIGS. 11A-C show another example of a tissue transfer device 800 of this disclosure. The device 800 may be substantially similar to the device 100 in design and use, except as described below. As shown in FIG. 11A, the device 800 may generally comprise a handle 801, a chisel in the form of an outer tube 804 coupled to the handle 801, an inner shaft 806 disposed within the outer tube 804, and a control mechanism, such as a screw mechanism 808, removeably coupled to the handle 801 to expel a tissue graft 118 in a controlled manner. In examples, the handle 801 may have a "T" shape with an elongated first portion 802 having a first surface 802*a* and a second surface 802*b* opposite the first surface 802*a*. A second portion 803 may extend perpendicular to the first portion 802 from an approximate center of the second surface 802*b*. The outer tube 804 may have a proximal end 804*a* coupled to the second portion 803 of the handle 801 and a distal end 804*b* configured for insertion into tissue. As shown in FIG. 11B, the inner shaft 806 may extend through the outer tube 804 such that a proximal end 806*a* of the inner shaft 806 projects from the first surface 802*a* of the handle 801. Examples of the screw mechanism 808 may include a screw body 816 extending through a housing 818 and configured to engage the proximal end 806*a* of the inner shaft 806. The housing 818 may removeably couple to the handle 801. A flange 820 may further couple to the screw body 816 and be configured to manually rotate the screw body 816 towards and away from the first surface 802*a* of the handle 801. Thus, rotation of the screw body 816 in a first direction may move the inner shaft 806 distally relative to the outer tube 804 to expel a tissue graft 118 from the outer tube 804 (FIG. 11C).

Figure 12A:
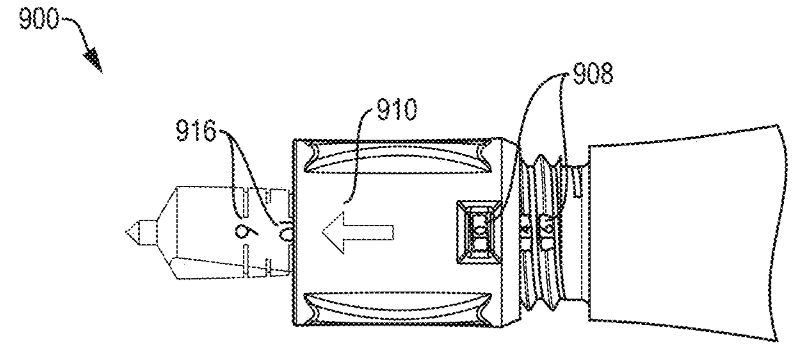
FIGS. 12A-C illustrate an example of an adjustable depth drill guide for creating a hole in an area of a tissue defect to a depth pre-selected to be equal to a length of a tissue graft.
Figure 12B:
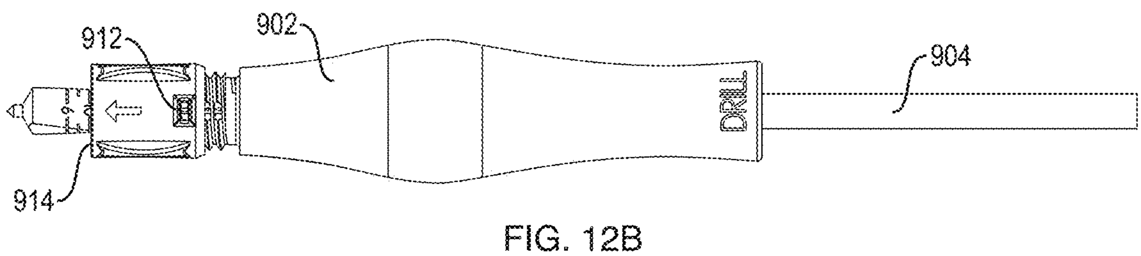
Figure 12C:
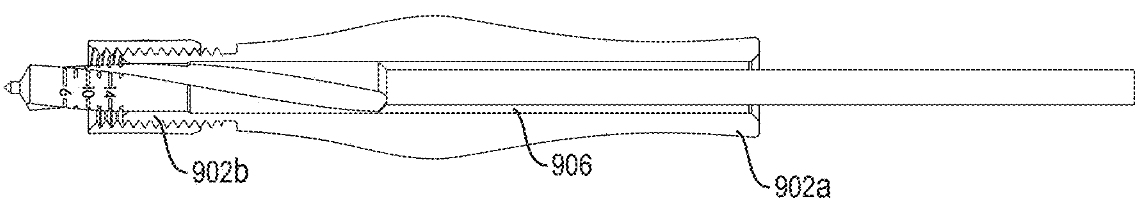

FIGS. 12A-C show an example of an adjustable depth drill guide 900 for creating a hole in an area of a tissue defect to a depth pre-selected to be equal to a length of a tissue graft. As shown in FIGS. 12A-C, a body 902 of the drill guide 900 defines a central cannulation 906 extending between a proximal end 902*a* and a threaded distal end 902*b* of the body 902 for receiving a drill 904. The threaded distal end 902*b* comprises indicia 908 on an outer surface thereof corresponding to markings 916 on a surface of the drill 904. A rotatable member 910 threadingly couples to the threaded distal end 902*b* and defines a window 912 through which the indicia 908 may be serially viewed. When a shoulder stop 914 of the rotatable member 910 aligns with one of the markings 916 on the drill 904, the corresponding indicia 908 on the threaded distal end 902*b* may be visible to the user through the window 912. Thus, the user can advantageously preselect a drill depth of the hole by drilling to the shoulder stop 914, without having to continuously read the markings 916 on the drill 904.

While the disclosure particularly shows and describes preferred examples, those skilled in the art will understand that various changes in form and details may exist without departing from the spirit and scope of the present application as defined by the appended claims. The scope of this present application intends to cover such variations. As such, the foregoing description of examples of the present application does not intend to limit the full scope conveyed by the appended claims.

The invention claimed is:

1. A tissue transfer device comprising:

a handle comprising a "T" shape and having a first surface and a second surface opposite the first surface, a through hole defined by the handle extending through a width of the handle;

an outer tube having a proximal end, a distal end, and a cannulation extending between the proximal and distal ends, the proximal end coupled to the second surface of the handle such that the cannulation extends in line with the through hole, the distal end configured for insertion into tissue;

an inner shaft extending through the cannulation of the outer tube such that a proximal end of the inner shaft projects from the first surface of the handle, the inner shaft axially moveable relative to the outer tube; and a control mechanism removably coupled to the handle in contact with the proximal end of the inner shaft, the control mechanism configured to move the inner shaft distally relative to the outer tube to expel a tissue graft from the outer tube.

2. The tissue transfer device of claim 1, wherein the control mechanism is a lever arm.

3. The tissue transfer device of claim 1, wherein the control mechanism is a ratchet mechanism.

4. The tissue transfer device of claim 1, wherein the control mechanism is a screw mechanism.

5. The tissue transfer device of claim 1, wherein the proximal end of the inner shaft comprises indicia corresponding to a length of the tissue graft.

6. The tissue transfer device of claim 1, wherein the distal end of the outer tube defines a window for direct visualization of the expulsion of the tissue graft.

7. The tissue transfer device of claim 1, wherein the inner shaft is removeable from the cannulation of the outer tube and configured to be used as a tamping tool.

8. The tissue transfer device of claim 1, wherein a diameter of the proximal end of the inner shaft is selected to be wider than an inner diameter of the cannulation such that, when the inner shaft is fully inserted into the outer tube, the proximal end contacts the first surface of the handle.

* * * * *